United States Patent
Ishikawa et al.

(10) Patent No.: US 11,622,851 B2
(45) Date of Patent: Apr. 11, 2023

(54) TORIC INTRAOCULAR LENS, INTRAOCULAR LENS INSERTION TOOL, AND METHOD FOR PRODUCING TORIC INTRAOCULAR LENS

(71) Applicant: Kowa Company, Ltd., Nagoya (JP)

(72) Inventors: Haruo Ishikawa, Nagoya (JP); Akemi Taniguchi, Nagoya (JP); Norio Shimizu, Nagoya (JP)

(73) Assignee: Kowa Company, Ltd., Nagoya (JP)

( * ) Notice: Subject to any disclaimer, the term of this patent is extended or adjusted under 35 U.S.C. 154(b) by 270 days.

(21) Appl. No.: 16/309,903

(22) PCT Filed: Jun. 14, 2017

(86) PCT No.: PCT/JP2017/021912
§ 371 (c)(1),
(2) Date: Dec. 13, 2018

(87) PCT Pub. No.: WO2017/217443
PCT Pub. Date: Dec. 21, 2017

(65) Prior Publication Data
US 2019/0167416 A1    Jun. 6, 2019

(30) Foreign Application Priority Data
Jun. 15, 2016  (JP) .............................. JP2016-119064

(51) Int. Cl.
*A61F 2/16* (2006.01)
(52) U.S. Cl.
CPC .............. *A61F 2/1645* (2015.04); *A61F 2/16* (2013.01); *A61F 2/167* (2013.01);
(Continued)

(58) Field of Classification Search
CPC .......... A61F 2/1645; A61F 2/16; A61F 2/167; A61F 2002/1683; A61F 2230/0065; A61F 2240/001; A61F 2250/0097
See application file for complete search history.

(56) References Cited

U.S. PATENT DOCUMENTS 6,024,448 A * 2/2000 Wu ................... B29D 11/00317
                                                351/159.69
9,277,988 B1 * 3/2016 Chu ....................... A61F 2/1613
(Continued)

FOREIGN PATENT DOCUMENTS

CN    105491981 A    4/2016
JP    4606594 B2     1/2011
(Continued)

OTHER PUBLICATIONS

Extended Search Report issued in the EP application No. 17813338.5, dated Feb. 12, 2020.
(Continued)

*Primary Examiner* — Leslie Lopez
(74) *Attorney, Agent, or Firm* — Knobbe, Martens, Olson & Bear, LLP

(57) ABSTRACT

There is provided a toric intraocular lens which improves the visibility of a toric axis. The toric intraocular lens is a toric intraocular lens including a lens body provided with an astigmatic axis. A mark indicating the astigmatic axis is formed at an optical surface of an outer rim portion of the lens body, and a length in a radial direction of the lens body and a length in a circumferential direction of the lens body of external dimensions of the mark are different from each other in top view of the optical surface.

7 Claims, 14 Drawing Sheets

(52) U.S. Cl.
CPC ............... *A61F 2002/1683* (2013.01); *A61F 2230/0065* (2013.01); *A61F 2240/001* (2013.01); *A61F 2250/0097* (2013.01)

(56) References Cited

U.S. PATENT DOCUMENTS

| | | | |
|---|---|---|---|
| 2002/0102415 A1* | 8/2002 | Valint, Jr. | C08L 83/10 351/159.33 |
| 2003/0224185 A1 | 12/2003 | Valint, Jr. et al. | |
| 2008/0281413 A1* | 11/2008 | Culbertson | A61F 2/1637 623/6.12 |
| 2011/0118836 A1* | 5/2011 | Jain | A61F 2/16 623/6.27 |
| 2014/0343541 A1* | 11/2014 | Scott | A61F 2/16 606/4 |
| 2016/0106534 A1 | 4/2016 | Deboer et al. | |
| 2016/0220349 A1 | 8/2016 | Wanders | |
| 2019/0231517 A1* | 8/2019 | Gengler | G02C 7/04 |
| 2019/0269551 A1 | 9/2019 | Scott et al. | |

FOREIGN PATENT DOCUMENTS

| | | |
|---|---|---|
| JP | 2011-245208 A | 12/2011 |
| JP | 2013-132503 A | 7/2013 |
| JP | 2014-014397 A | 1/2014 |
| JP | 5771907 B2 | 9/2015 |
| WO | WO 2009/137491 A1 | 11/2009 |
| WO | WO 2015/037994 A1 | 3/2015 |
| WO | WO 2016/034925 A1 | 3/2016 |

OTHER PUBLICATIONS

International Search Report issued in application No. PCT/JP2017/021912, dated Jul. 25, 2017.
International Preliminary Report on Patentablity issued in application No. PCT/JP2017/021912, dated Dec. 27, 2018.
Office Action issued in CN application No. 201780037165.8, dated Apr. 20, 2020.
Notice of Preliminary Rejection dated Dec. 7, 2021, in corresponding KR Application No. 10-2018-7035857.

* cited by examiner

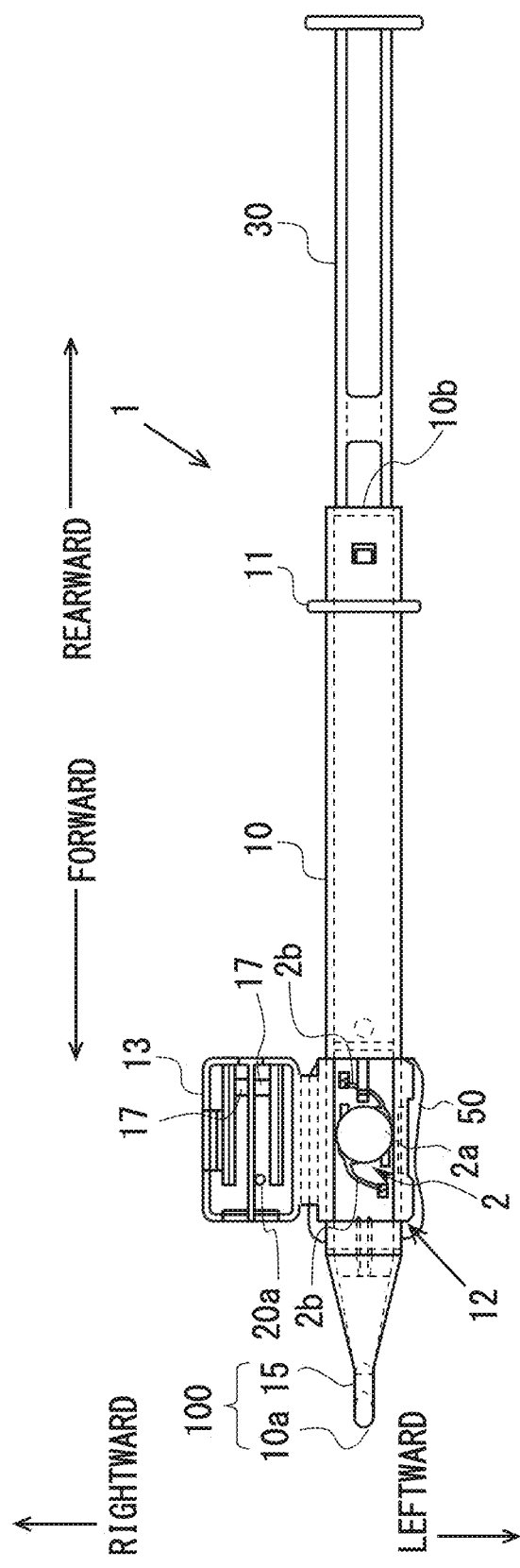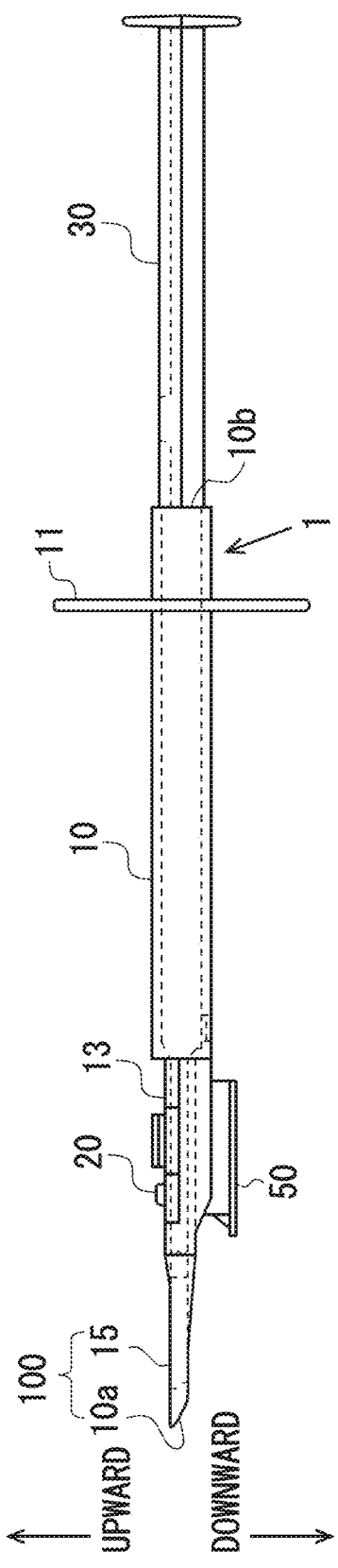

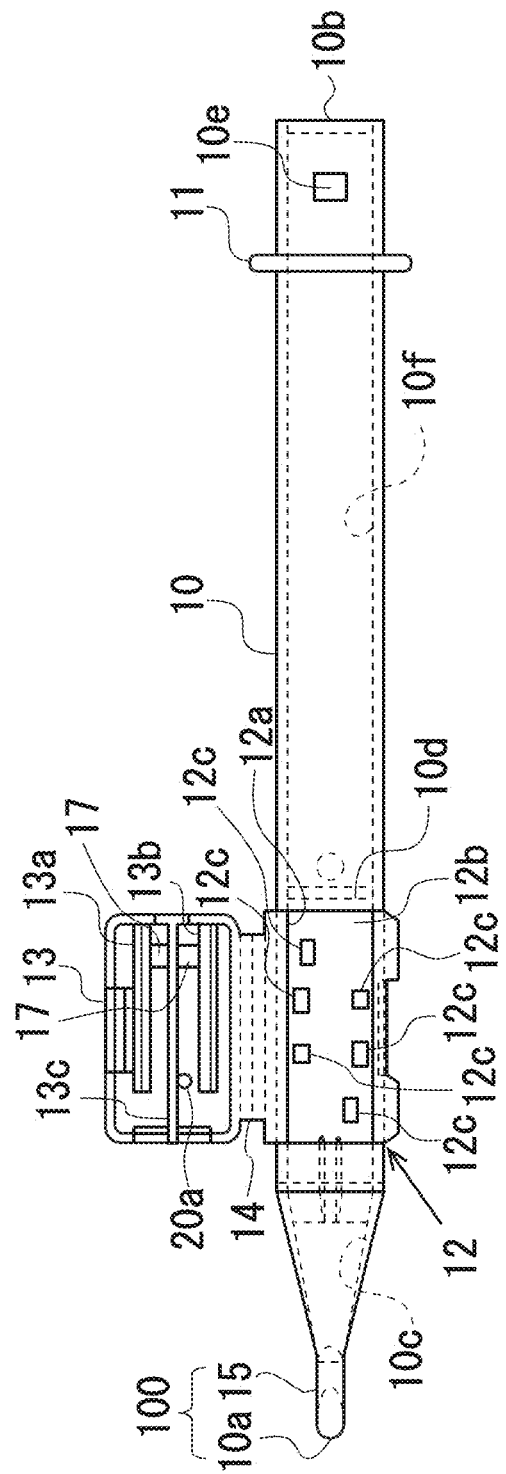

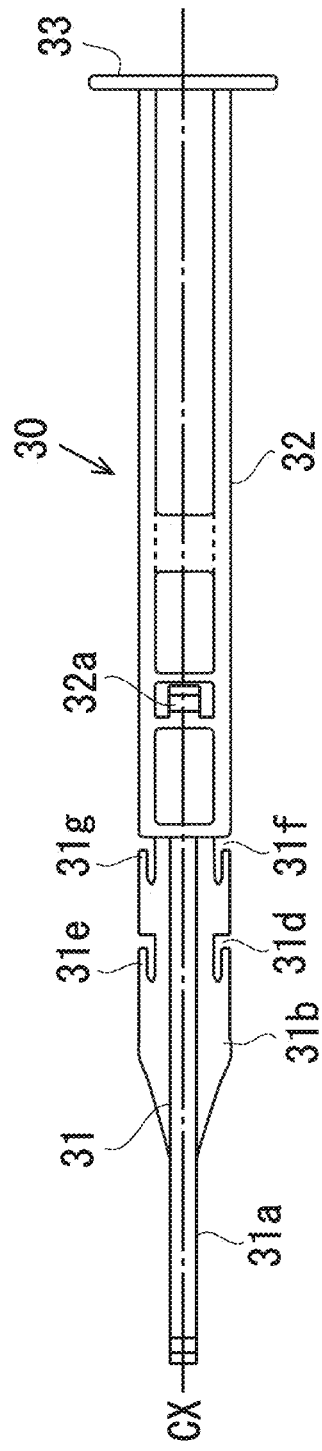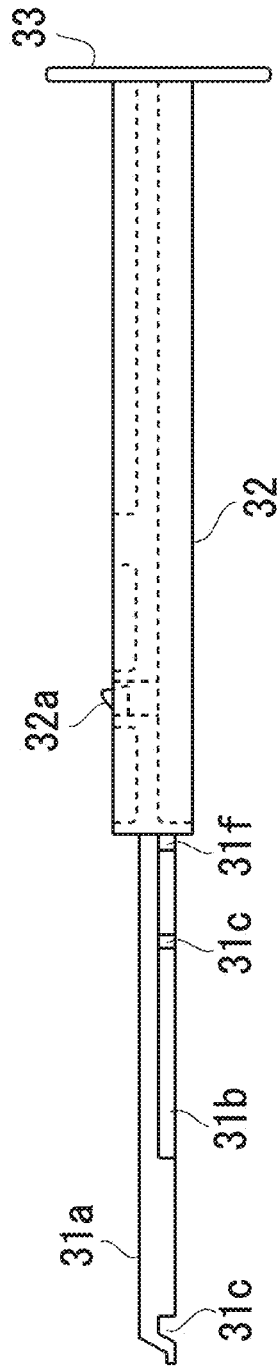

TORIC INTRAOCULAR LENS, INTRAOCULAR LENS INSERTION TOOL, AND METHOD FOR PRODUCING TORIC INTRAOCULAR LENS

FIELD

The present invention relates to a toric intraocular lens, an intraocular lens insertion tool, and a manufacturing method for a toric intraocular lens.

BACKGROUND

In cataract therapy, an intraocular lens which is inserted as a substitute for a crystalline lens to replace an opaque crystalline lens of a human eye or compensate the refraction has been put to practical use. When a patient with corneal astigmatism undergoes a cataract operation, an intraocular lens capable of correcting astigmatism, i.e., a toric intraocular lens may be inserted. After the toric intraocular lens is inserted into an eyeball of the patient, an astigmatic axis of a cornea of the patient needs to be made to coincide with a toric axis of the intraocular lens.

A conventional toric intraocular lens has a plurality of circular dots in a straight line which are put as marks indicating a toric axis (a steep meridian or a flat meridian). The toric intraocular lens includes a lens body which has predetermined refractive power and support portions for retaining the lens body in an eyeball which are coupled to the lens body. The marks indicating the toric axis are put in the vicinities of respective connecting portions for the support portions in the lens body (e.g., Patent document 1).

CITATION LIST

Patent Literature

[PTL 1] JP-B-5771907

SUMMARY

Technical Problem

The marks indicating the toric axis are formed on the toric axis (an astigmatic axis) at an anterior surface of the lens body, e.g., by printing or so as to have an uneven shape. However, a mark printed on a lens body may be mistaken for a line or the like generated in a crystalline lens of a patient. A mark formed so as to have a circular shape, a spherical shape, or the like at a lens body may be mistaken for an air bubble or the like which has got mixed in an eyeball at the time of operation. In a case of a small pupil, an IOL (Intraocular Lens) is inserted into a back side of the pupil as viewed from an operator, and the operator may be able to observe one mark alone. In this case, it is difficult for the operator to accurately recognize the toric axis by a circular mark or a spherical mark. Furthermore, by forming a mark with a roughened surface and scattering light with the rough surface, the appearance may be made different for the operator between a part marked on a lens body and a part not marked on the lens body. Light scattered by a rough surface, however, is likely to become stray light and may influence the visual performance of the patient.

A technique according to the present disclosure has been made in view of the above-described circumstances, and has as its object to provide a toric intraocular lens which improves the visibility of a toric axis.

Solution to Problem

A toric intraocular lens according to the present disclosure is a toric intraocular lens including a lens body provided with an astigmatic axis, wherein a mark indicating the astigmatic axis is formed at an optical surface of the lens body, and a length in a radial direction of the lens body and a length in a circumferential direction of the lens body of external dimensions of the mark are different from each other in top view of the optical surface. With this configuration, how light reflects changes at a boundary between the mark and the optical surface. Even if an operator can visually recognize a part alone of the mark after the toric intraocular lens is inserted into an eyeball of a patient, the operator can identify the astigmatic axis on the basis of the mark. Additionally, the possibility of the mark being mistaken for an air bubble mixed in the eyeball is reduced.

In the toric intraocular lens, a contour of a rim of the mark at least on one end side of a first axis extending in the radial direction of the lens body in the mark may not have an arc of a perfect circle. Also, the mark may be a recessed portion that is formed at a posterior surface of the lens body or a projecting portion that is formed at an anterior surface of the lens body. Additionally, a radial dimension of a chamfer at the rim of the mark in a cross-section of the lens body along a plane parallel to an optical axis of the lens body may be 0.1 mm or a smaller dimension. Moreover, the rim may be composed of the optical surface and a slope of the mark. Alternatively, a peripheral portion of the mark may be adapted to change in brightness a stepwise manner. With this configuration, the mark and an optical portion other than the mark are different for an operator in how light reflects and in appearance, and the visibility of the mark of the lens body is improved.

The mark may include an inclined surface adjacent to the rim in the cross-section of the lens body along the plane parallel to the optical axis of the lens body. Also, a value of surface roughness of the mark may be 20 nm or a smaller value, and surface roughness of the optical surface may be different from the surface roughness of the mark. Additionally, the toric intraocular lens may constitute a toric intraocular lens group that is composed of a plurality of toric intraocular lenses different in refractive power of the lens body, and the mark may be provided at a fixed position relative to a position of a support portion of the toric intraocular lens in each of the toric intraocular lenses in the toric intraocular lens group, regardless of the refractive power of the lens body. Moreover, the mark may be provided at a fixed position relative to a position of a support portion of the toric intraocular lens, regardless of the refractive power of the lens body.

Alternatively, the above-described toric intraocular lens may be housed in advance in an intraocular lens insertion tool for inserting a toric intraocular lens into an eye of a patient. A manufacturing method for the above-described toric intraocular lens may include polymerizing resin to constitute the lens body, using a mold with an indicator put to provide a position of the mark indicating the astigmatic axis at the fixed position relative to the position of the support portion of the toric intraocular lens. The indicator of the resin mold may be a recessed portion or surface roughness of the indicator of the resin mold may be different from surface roughness of a portion other than the indicator.

Advantageous Effects of Invention

The technique according to the present disclosure allows provision of a tonic intraocular lens which improves the visibility of a tonic axis.

BRIEF DESCRIPTION OF DRAWINGS

FIG. 2A is a first view illustrating a schematic configuration of an intraocular lens insertion tool according to the one embodiment.

FIG. 2B is a second view illustrating a schematic configuration of an intraocular lens insertion tool according to the one embodiment.

FIG. 3 is a view illustrating a schematic configuration of a nozzle body according to the one embodiment.

FIG. 5A is a first view illustrating a schematic configuration of a plunger according to the one embodiment.

FIG. 5B is a second view illustrating a schematic configuration of a plunger according to the one embodiment.

DESCRIPTION OF EMBODIMENTS

An embodiment of the present invention will be described below with reference to the drawings.

Figure 1A:
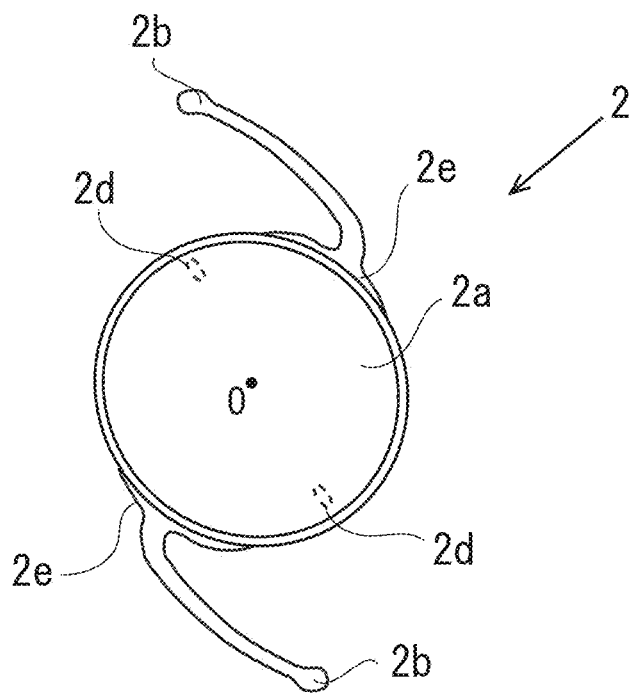
FIG. 1A is a first view illustrating a schematic configuration of a toric intraocular lens according to one embodiment.
Figure 1B:
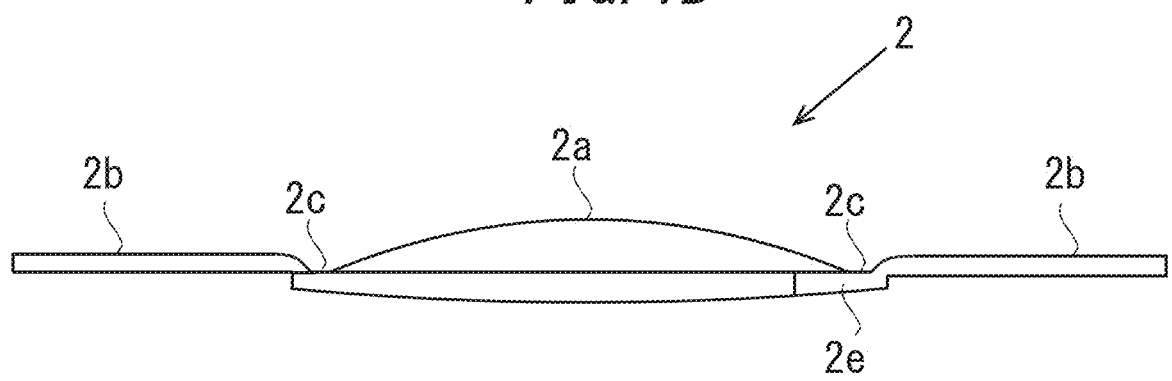
FIG. 1B is a second view illustrating a schematic configuration of a toric intraocular lens according to one embodiment.
Figure 1C:
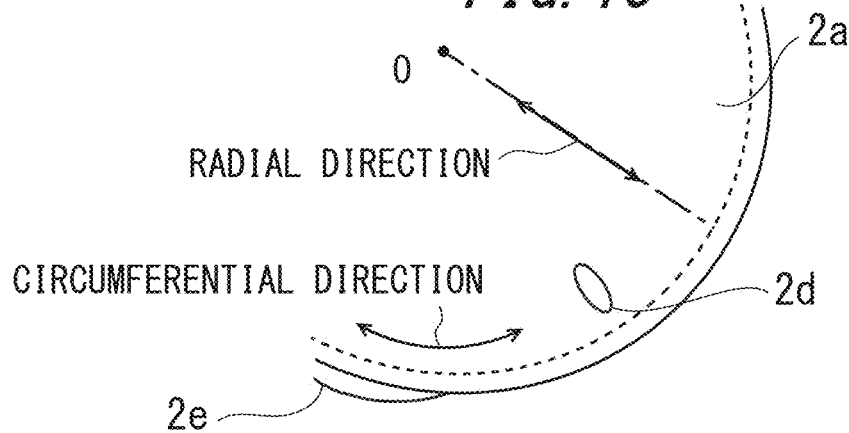
FIG. 1C is a third view illustrating a schematic configuration of a toric intraocular lens according to one embodiment.

FIGS. 1A to 1C are a set of views illustrating a schematic configuration of a toric intraocular lens 2 according to the present embodiment. FIG. 1A is a plan view, FIG. 1B is a side view, and FIG. 1C is an enlarged view of the vicinity of a mark. Note that FIG. 1A and FIG. 1B are different in the orientation of the toric intraocular lens 2. FIG. 1C is a top view of the mark as viewed from a side opposite to that in FIG. 1A, i.e., a posterior surface side of the intraocular lens. The toric intraocular lens 2 is of a so-called one-piece type in which a lens portion and support portions are integrally formed of the same material, and a material for the lens is a soft acrylic material. The toric intraocular lens 2 includes a lens body 2a which has predetermined refractive power and two support portions 2b in the shape of an elongated flat plate for retaining the lens body 2a in an eyeball which are coupled to the lens body 2a. The lens body 2a and the support portions 2b are formed of a flexible resin material. The lens body 2a and the support portions 2b are connected to each other via connecting portions 2e.

As illustrated in FIG. 1B, each connecting portion 2e is formed to extend from a lens outer peripheral surface in the shape of a tangential line and is provided in contact with an outer periphery of the lens body 2a over a predetermined range. In the present embodiment, one pair of marks 2d which face each other across an optical axis O of the lens body 2a is put in the vicinity of an outer rim portion of an optical surface of the lens body 2a. The marks are preferably located away from the optical axis O by 1.5 mm or more, more preferably 2.0 mm or more. An imaginary line connecting the marks 2d represents a first axis (e.g., a flat meridian) of the lens body 2a, and a line which crosses the imaginary line at right angles at the optical axis O of the lens body 2a represents a second axis (e.g., a steep meridian). An operator is thus capable of adjusting the position of the toric intraocular lens 2 such that a steep meridian direction of a cornea of a patient coincides with a flat meridian direction represented by the marks 2d of the lens body 2a after inserting the toric intraocular lens 2 into an eyeball of the patient. Note that details of a configuration of the mark 2d will be described later.

In the present embodiment, inside an intraocular lens insertion tool 1 (to be described later), the toric intraocular lens 2 is set on a stage member 12 such that one support portion 2b of the two support portions 2b is arranged on a rear side of the lens body 2a and such that the other support portion 2b is arranged on a front side of the lens body 2a. Note that the support portion arranged on the front side of the lens body 2a is referred to as a front support portion while the support portion arranged on the rear side of the lens body 2a is referred to as a rear support portion.

In the toric intraocular lens 2 according to the present embodiment, the support portions 2b are grained. This allows stabilization of the posture of the toric intraocular lens 2 at the time of pressing and movement of the toric intraocular lens 2 by a plunger 30. More specifically, moderate frictional force generated between the support portions 2b and an inner wall surface of a nozzle body 10 when the toric intraocular lens 2 is pressed and moved by the plunger 30 can prevent the toric intraocular lens 2 from rotating inside the nozzle body 10. Since the support portions 2b are grained, the support portions 2b can be prevented from sticking to the lens body 2a when the toric intraocular lens 2 is folded inside the nozzle body 10. In the present embodiment, as illustrated in FIG. 1B, a small-curvature optical surface 2c which moderates the tilt of the optical surface of the lens body 2a is provided at a peripheral portion of the lens body 2a of the toric intraocular lens 2, i.e., a coupling portion between the lens body 2a and the support portions 2b, which reduces a lens center thickness and a lens cross-sectional area. This implements a thin lens shape. The optical surface 2c here may have a flat shape.

Note that since an optical portion diameter of an anterior surface is slightly larger within the ranges where the connecting portions 2e are in contact with the outer periphery of the lens body 2a than within a range other than the ranges by an amount corresponding to a processing margin, an optical portion is slightly elliptical (non-circular) at the anterior surface. A posterior surface optical portion has an optical portion diameter larger within the ranges where the connecting portions 2e are in contact with the outer periphery of the lens body 2a than within a range other than the ranges by about 10%, i.e., each connecting portion 2e also has a portion having a function of an optical lens surface. With this configuration, a lens effective range is widened even to a small extent within predetermined dimensions defined for the lens body 2a. Generally, an optical portion diameter of the lens body 2a within a range where the lens body 2a is not in contact with the connecting portions 2e is 5.5 mm to 7.0 mm.

FIGS. 2A and 2B illustrate a schematic configuration of the intraocular lens insertion tool 1 that is used to insert a toric intraocular lens according to the present embodiment into an eye. FIG. 2A illustrates a plan view of the intraocular lens insertion tool 1 when a stage lid member 13 is opened, and FIG. 2B illustrates a side view of the intraocular lens insertion tool 1 when the stage lid member 13 is closed. The nozzle body 10 of the intraocular lens insertion tool 1 is a tubular member which is almost rectangular in cross-section and includes a rear end portion 10b which has a wide opening at an end portion on one side, and a nozzle portion 15 and a distal end portion 10a as a narrowed insertion tube 100 at an end portion on a different side. As illustrated in FIG. 2B, the distal end portion 10a has an oblique opening. The plunger 30 is inserted into the nozzle body 10 and is capable of reciprocation.

In the following description, a direction from the rear end portion 10b of the nozzle body 10 toward the distal end portion 10a is referred to as a forward direction, the opposite direction is referred to as a rearward direction, a near side of the sheet surface in FIG. 2A is referred to as an upward direction, the opposite direction is referred to as a downward direction, a direction toward a near side of the sheet surface in FIG. 2B is referred to as a leftward direction, and the opposite direction is referred to as a rightward direction. In this case, an upper side corresponds to an optical axis front side of the lens body 2a (to be described later), a lower side corresponds to an optical axis rear side of the lens body 2a, a front side corresponds to a front side in a direction of pressing by the plunger 30, and a rear side corresponds to a rear side in the direction of pressing by the plunger 30.

A hold member 11 which projects like a plate shape and on which a user hooks fingers at the time of pushing the plunger 30 toward a distal end side of the nozzle body 10 is integrally provided in the vicinity of the rear end portion 10b of the nozzle body 10. The stage member 12, on which the toric intraocular lens 2 is to be set, is provided on the rear side of the nozzle portion 15 in the nozzle body 10. The stage member 12 opens to the upper side of the no body 10 by opening the stage lid member 13. A positioning member 50 is attached to the stage member 12 from the lower side of the nozzle body 10. With the positioning member 50, the toric intraocular lens 2 is stably positioned on the stage member 12 even before use (in transit).

That is, in the intraocular lens insertion tool 1 at the time of manufacture, the toric intraocular lens 2 is set on the stage member 12 with the optical axis front side facing upward while the stage lid member 13 opened, and the positioning member 50 is attached to the stage member 12. After the stage lid member 13 is closed, the intraocular lens insertion tool 1 is shipped and sold. Additionally, when used, a user inserts a needle of a syringe filled with a lubricant agent for a toric intraocular lens into the stage member 12 through a needle hole 20a of an insertion portion 20 and injects the lubricant agent. The user removes the positioning member 50 with the stage lid member 13 closed and then pushes the plunger 30 toward the distal end side of the nozzle body 10.

With the above-described operations, the toric intraocular lens 2 is pressed by the plunger 30 and is moved to the nozzle portion 15. In this state, the toric intraocular lens 2 is released from the distal end portion 10a into an eyeball. Note that the nozzle body 10, the plunger 30, and the positioning member 50 in the intraocular lens insertion tool 1 are formed of a resin material, such as polypropylene. Polypropylene is a material which has a track record for medical instruments and is high in reliability, such as chemical resistance.

Check windows 17 are formed by thinning parts of the stage lid member 13. Note that to what extent the check windows 17 are thinned in the stage lid member 13 may be appropriately determined on the basis of a material for forming the stage lid member 13 and the visibility of a toric intraocular lens from the check windows 17. The effect of reducing sink marks at the time of molding of the stage lid member 13 can be expected by forming the check windows 17.

FIG. 3 illustrates a plan view of the nozzle body 10. As described earlier, in the nozzle body 10, the toric intraocular lens 2 is set on the stage member 12. The toric intraocular lens 2 is pressed by the plunger 30 in this state and is released from the distal end portion 10a. Note that a through-hole 10c on the distal end side and a through-hole 10f on a rear end side which change in cross-sectional shape in response to a change in an outer shape of the nozzle body 10 are provided inside the nozzle body 10. The through-hole 10c is a hole which serves as a part of a movement path when the toric intraocular lens 2 is pressed and moved, and the through-hole 10f is a hole into which the plunger 30 is inserted. When the toric intraocular lens 2 is to be released, the toric intraocular lens 2 changes in shape in response to a change in the cross-sectional shape of the through-hole 10c inside the nozzle body 10, and is changed in shape to a shape easily accessible to an incisional wound produced in an eyeball of a patient and is released.

The distal end portion 100 has a so-called bevel-cut shape in which the distal end portion 10a is obliquely cut such that an upper region of the nozzle portion 15 extends to a side in front of a lower region. Note that although details of a distal end of the nozzle portion 15 according to the present embodiment will be described later, the distal end portion 10a may be linearly and obliquely cut as viewed from the leftward and rightward directions or may be cut obliquely so as to have an outward bulge, i.e., have a curved shape, as for the obliquely cut shape of the distal end portion 10a.

A stage groove 12a which has a width slightly larger than a diameter of the lens body 2a of the toric intraocular lens 2 is formed in the stage member 12. A dimension in the forward and rearward directions of the stage groove 12a is set larger than a maximum width dimension including the support portions 2b extending on two sides of the toric intraocular lens 2. A bottom surface of the stage groove 12a forms a set surface 12b which is a mounting surface for a toric intraocular lens. A position in the upward and downward directions of the set surface 12b is set above a height position of a bottom surface of the through-hole 10f in the nozzle body 10, and the set surface 12b and the bottom surface of the through-hole 10f are coupled by a bottom inclined surface 10d.

The stage member 12 and the stage lid member 13 are integrally formed. The stage lid member 13 has a dimension in the forward and rearward directions equivalent to that of the stage member 12. The stage lid member 13 is connected by a connection member 14 in the shape of a thin plate which is formed from a side surface of the stage member 12 extending toward the stage lid member 13. The connection member 14 is formed to be bendable at a center positon. The stage lid member 13 can lie over the stage member 12 from the upper side and be closed by bending the connection member 14.

In the stage lid member 13, ribs 13a and 13b for reinforcing the stage lid member 13 and stabilizing the position of the toric intraocular lens 2 and a guide projection 13c as an upper guide for the plunger 30 are provided at a surface which faces the set surface 12b when the stage lid member 13 is closed. The needle hole 20a as an insertion hole for injecting hyaluronic acid into the stage member 12 by a syringe before the work of inserting the toric intraocular lens 2 into an eyeball is provided in the stage lid member 13. The needle hole 20a is a hole which connects an outside of the stage member 12 and the toric intraocular lens 2 housed in the stage member 12 when the stage lid member 13 is closed. A user inserts a needle of a syringe through the needle hole 20a before the work of inserting the toric intraocular lens 2 and supplies hyaluronic acid that is a viscoelastic substance to a needed position inside the stage member 12.

The positioning member 50 is removably provided on the lower side of the set surface 12b of the stage member 12.

Figure 4A:
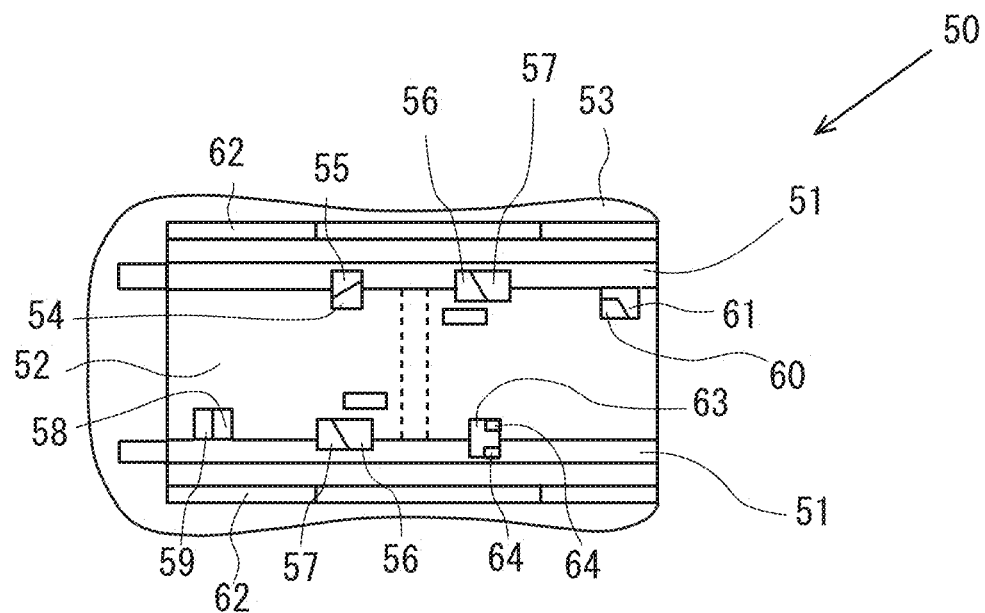
FIG. 4A is a first view illustrating a schematic configuration of a positioning member according to the one embodiment.
Figure 4B:
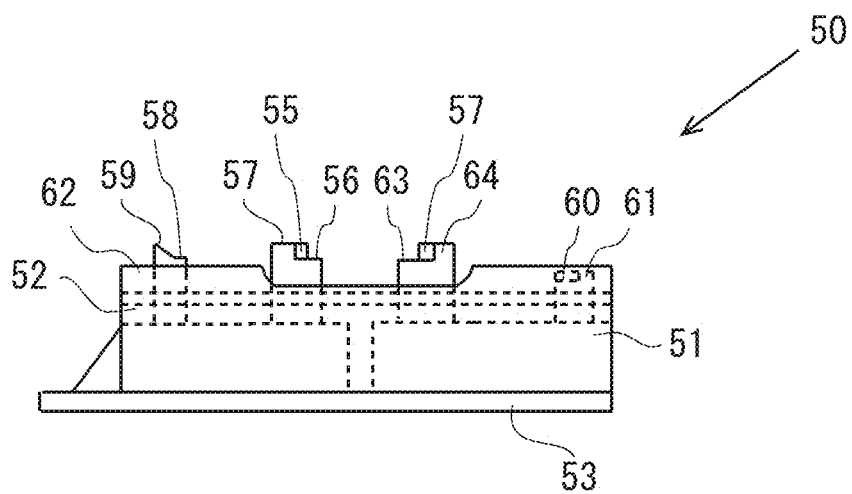
FIG. 4B is a second view illustrating a schematic configuration of a positioning member according to the one embodiment.

FIGS. 4A and 4B illustrate a schematic configuration of the positioning member 50. FIG. 4A illustrates a plan view of the positioning member 50, and FIG. 4B illustrates a left side view of the positioning member 50. The positioning member 50 is constructed separately from the nozzle body 10 and has a structure in which one pair of side wall portions 51 and 51 is connected by a connecting portion 52. A holding portion 53 which extends outward and spreads is formed at a lower end of the side wall portions 51.

A first mounting portion 54 and a second mounting portion 63 which protrude upward are formed inside the side wall portions 51 and 51. A first positioning portion 55 is further formed to protrude on an outer periphery side at an upper end face of the first mounting portion 54. One pair of second positioning portions 64 which position the lens body 2a and the support portion 2b of the intraocular lens 2 is formed to protrude at an upper end face of the second mounting portion 63. A separation distance between the first positioning portion 55 and the second positioning portions 64 is set slightly larger than a diametrical dimension of the lens body 2a of the intraocular lens 2.

Also, one pair of third mounting portions 56 and 56 which protrude upward is formed inside the side wall portions 51 and 51. Heights of upper surfaces of the first mounting portion 54, the second mounting portion 63, and the third mounting portions 56 and 56 are equivalent to one another. Third positioning portions 57 and 57 which each protrude upward over a whole in the leftward and rightward directions a corresponding one of the third mounting portions 56 and 56 are further formed at outer portions of the upper surfaces of the third mounting portions 56 and 56. separation distance between inner sides of the third positioning portions 57 and 57 is set slightly larger than the diametrical dimension of the lens body 2a of the intraocular lens 2.

Additionally, a fourth mounting portion 58, on which a part of the front support portion of the support portions 2b of the intraocular lens 2 is mounted, is formed inside the side wall portions 51 and 51. A fourth positioning portion 59 which protrudes upward from the fourth mounting portion 58 is further formed. The part of the front support portion abuts on the fourth positioning portion 59. A fifth mounting portion 60, on which a part of the rear support portion of the support portions 2b of the intraocular lens 2 is mounted, is formed inside the side wall portions 51 and 51. A fifth positioning portion 61 which protrudes upward from the fifth mounting portion 60 is further formed. The part of the rear support portion abuts on the fifth positioning portion 61.

Note that, as illustrated in FIG. 4B, the fifth mounting portion 60 and the fifth positioning portion 61 are provided such that heights of upper surfaces of the fifth mounting portion 60 and the fifth positioning portion 61 are lower than heights of upper surfaces of the first to fourth mounting portions and the first to fourth positioning portions. Anti-rotation wall portions 62 for preventing unnecessary rotation at the time of removing the positioning member 50 are provided outside the side wall portions 51 and 51.

Set surface through-holes 12c which extend through the set surface 12b in a thickness direction are formed in the set surface 12b of the nozzle body 10. Outer shapes of the set surface through-holes 12c are shapes slightly larger than and almost similar to the shapes of the first to fifth mounting portions and the first to fifth positioning portions of the positioning member 50 as viewed from the upper side. When the positioning member 50 is attached to the nozzle body 10, the first to fifth mounting portions and the first to fifth positioning portions are inserted into the set surface through-holes 12c from the lower side of the set surface 12b and protrude upward from the set surface 12b.

When the intraocular lens 2 is set on the set surface 12b, an outer peripheral portion bottom surface of the lens body 2a is mounted on the upper surfaces of the first mounting portion 54, the second mounting portion 63, and the third mounting portions 56 and 56. The lens body 2a is position-regulated in a horizontal direction (a direction horizontal to the set surface 12b) by the first positioning portion 55, the second positioning portions 64, and the third positioning portions 57 and 57. Additionally, the two support portions 2b of the intraocular lens 2 are mounted on the respective upper surfaces of the fourth mounting portion 58 and the fifth mounting portion 60. The two support portions 2b are position-regulated in the horizontal direction by the fourth positioning portion 59 and the fifth positioning portion 61, respectively.

FIGS. 5A and 5B illustrate a schematic configuration of the plunger 30. The plunger 30 has a length in the forward and rearward directions somewhat larger than that of the nozzle body 10. The plunger 30 is formed from a working member 31 on a distal end side based on a circular cylinder shape and an insertion member 32 to be inserted on a rear end side based on a rectangular rod shape. The working member 31 includes a circular columnar portion 31a in a circular cylindrical shape and flat portions 31b in the shape of a thin plate which spread in the leftward and rightward directions of the circular columnar portion 31a. FIG. 5A illustrates a center axis CX of the working member 31 (the circular columnar portion 31a) of the plunger 30. A distal end of the plunger 30 here generally has a width (thickness) of 0.5 mm to 2.0 mm. If the distal end is thinner, plunger strength is too low to stably push a lens. On the other hand, if the distal end is thicker, a wound for inserting an intraocular lens into an eye is larger, astigmatism called surgically induced astigmatism may occur to adversely influence the visual performance.

A notch 31c is formed in a distal end portion of the working member 31. As can be seen from FIG. 5B, the notch 31c opens in the downward direction in the working member 31 and is formed in the shape of a groove which extends in the leftward and rightward direction. As can be seen from FIG. 5B, a groove wall on a distal end side of the notch 31c is formed from an inclined surface which extends downward toward the distal end side of the working member 31.

Slits 31d and 31f are formed halfway and in the vicinity of a proximal end in the forward and rearward directions of each of the left and right flat portions 31b. The slits 31d and 31f are each formed in an almost L-shape which is composed of an incision extending in the leftward and rightward directions in the flat portion 31b and an incision extending in the forward and rearward directions. The formation of the slits 31d and 31f in each flat portion 31b causes formation of movable pieces 31e and 31g. The movable pieces 31e and 31f fulfill a so-called axis-shift prevention function such that the circular columnar portion 31a is located at the middle in the leftward and rightward directions of the nozzle body 10 when the plunger 30 moves inside the nozzle body 10. Although the two pairs of movable pieces 31e and 31g are formed in the present embodiment, one pair alone or three or more pairs may be formed.

The insertion member 32 to be inserted has a cross-section in an almost H-shape overall, and dimensions in the leftward and rightward directions and in the upward and downward directions are set slightly smaller than those of the through-hole 10f in the nozzle body 10. A pressing plate member 33 in a disk shape which spreads in the upward, downward, leftward, and rightward directions is formed at a rear end of the insertion member 32.

A pawl portion 32a which protrudes upward from the insertion member 32 to be inserted and is vertically movable due to elasticity of a material for the plunger 30 is formed at a portion closer to a tip than a middle in the forward and rearward directions of the insertion member 32. When the plunger 30 is inserted into the nozzle body 10, the pawl portion 32a engages with a locking hole 10e illustrated in FIG. 3 which is provided in the thickness direction in an upper surface of the nozzle body 10. With the engagement, positions of the nozzle body 10 and the plunger 30 relative to each other in an initial state are determined. Note that formation positions of the pawl portion 32a and the locking hole 10e are set such that, in an engaged state, a distal end of the working member 31 is located on the rear side of the lens body 2a of the toric intraocular lens 2 set on the stage member 12 and is located in a place where the notch 31c can hold the support portion 2b on the rear side of the lens body 2a from above. In the insertion member 32 as well, a slit in an almost L-shape which is composed of an incision extending in the leftward and rightward directions and an incision extending in the forward and rearward directions, like the slits 31d and 31f, may be formed. The slit thus formed in the insertion member 32 to be inserted also fulfills the function of preventing axis-shift of the plunger 30.

A manufacturing method for an intraocular lens according to the present embodiment will be described.

Figure 6A:
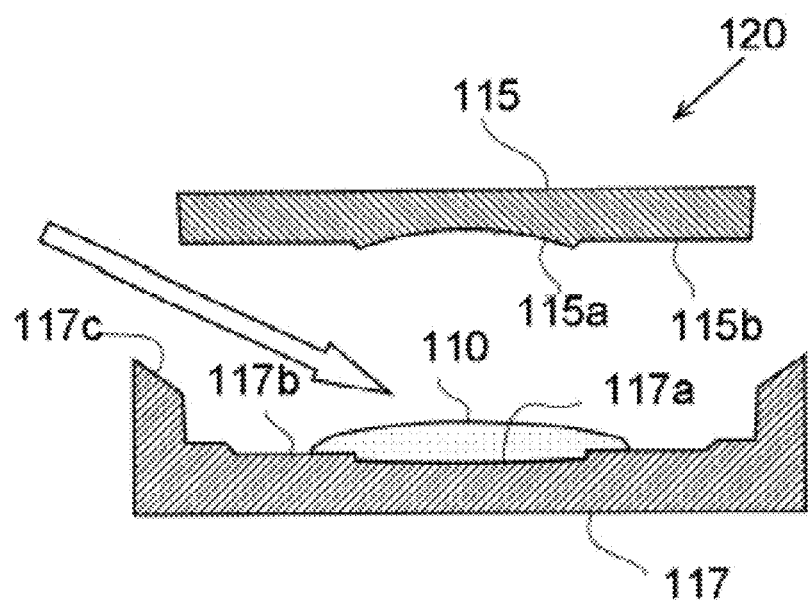
FIG. 6A is a first schematic view illustrating molding of a bulk intraocular lens according to the one embodiment.
Figure 6B:
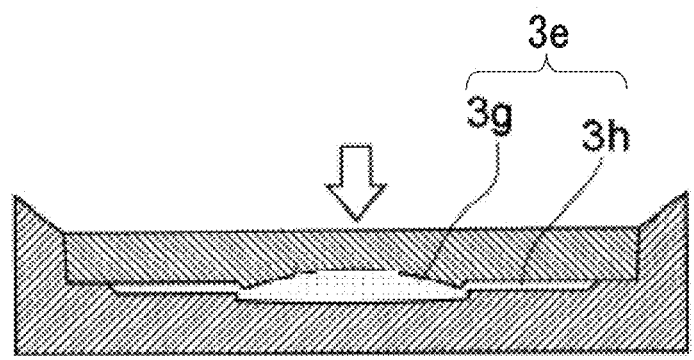
FIG. 6B is a second schematic view illustrating molding of a bulk intraocular lens according to the one embodiment.

A process of manufacturing a bulk intraocular lens 3e which is a base for an intraocular lens according to the present embodiment will be described in detail with reference to FIGS. 6A to 10B. FIGS. 6A and 6B illustrate schematic views of a resin mold 120 for molding for the bulk intraocular lens 3e. The resin mold 120 for molding is composed of an upper resin mold 115 and a lower resin mold 117. The bulk intraocular lens 3e that is a base for an intraocular lens 2 is molded by bringing the upper resin mold 115 and the lower resin mold 117 together and filling a void formed between the upper resin mold 115 and the lower resin mold 117 with a soft material. FIG. 6A is a cross-sectional view illustrating a state in which the upper resin mold 115 and the lower resin mold 117 are separated. FIG. 6B is a cross-sectional view illustrating a state during the molding of the bulk intraocular lens 3e by bringing the upper resin mold 115 and the lower resin mold 117 together. The bulk intraocular lens 3e includes a pre-lens body 3g and a pre-support portion 3h. Details of the pre-lens body 3g and the pre-support portion 3h will be described later.

As illustrated in FIG. 6A, the upper resin mold 115 has an optical portion anterior surface molding portion 115a for forming an anterior surface of a lens body 3a of the bulk intraocular lens 3e and a support portion anterior surface molding portion 115b for molding an anterior surface of a portion which is to serve as support portions portions 3b. The lower resin mold 117 has an optical portion posterior surface molding portion 117a for forming an optical portion posterior surface in the lens body 3a of the bulk intraocular lens 3e and a support portion posterior surface molding portion 117b for molding a posterior surface of the portion that is to serve as the support portions 3b. The lower resin mold 117 is also provided with an outer wall portion 117c which is provided over a whole outer periphery of the lower resin mold 117 and is intended to be brought together with the upper resin mold 115.

The upper resin mold 115 and the lower resin mold 117 are formed by injection molding, and a general-purpose resin material is used as a material. A plastic resin which is free of deformation due to a raw material monomer as a lens material and is excellent in solvent resistance is desirable as the resin material, and the upper resin mold 115 and the lower resin mold 117 may be polymerization vessels made of a polyolefin resin, such as polyethylene or polypropylene. The upper resin mold 115 and the lower resin mold 117 may be molded using an acrylic resin, such as PMMA, a nylon resin, or the like.

At the time of manufacturing the intraocular lens 2 using the above-described resin mold 120 for injection molding, a raw material monomer 110 as a lens material is supplied to the lower resin mold 117, as illustrated in FIG. 6A. The raw material monomer 110 may be one generally used for an intraocular lens and is not particularly limited. A publicly known thermopolymerization initiator, a publicly known photopolymerization initiator, or the like can be used as a polymerization initiator. In order to make the intraocular lens 2 UV-resistant by imparting ultraviolet absorbing power to the intraocular lens 2 or coloring the intraocular lens 2, a polymerizable ultraviolet absorbing agent, a polymerizable dye, or the like may be used as a copolymerization component.

As illustrated in FIG. 6B, the upper resin mold 115 and the lower resin mold 117 are brought together by fitting the upper resin mold 115 into the outer wall portion 117c of the lower resin mold 117. With this operation, a void surrounded by the optical portion anterior surface molding portion 115a of the upper resin mold 115 and the optical portion posterior surface molding portion 117a of the lower resin mold 117 is filled with the raw material monomer 110 to form a portion corresponding to the lens body 3a, and a void surrounded by the support portion anterior surface molding portion 115b of the upper resin mold 115 and the support portion posterior surface molding portion 117b of the lower resin mold 117 is filled with the raw material monomer 110 to form a portion corresponding to the support portions 3b. With this operation, a void surrounded by the optical portion anterior surface molding portion 115a of the upper resin mold 115 and the optical portion posterior surface molding portion 117a of the lower resin mold 117 is filled with the raw material monomer 100 to form a portion corresponding to the lens body 3a, and a void surrounded by the support portion molding portion 115b of the upper resin mold 115 and the support portion molding portion 117b of the lower resin mold 117 is filled with the raw material monomer 110 to form a portion corresponding to the support portions 3b.

The raw material monomer 110, with which a void between the upper resin mold 115 and the lower resin mold 117 is filled, is polymerized inside the resin mold 120 for molding. For example, heat polymerization that, in stepwise manner or continuously, raises temperature within a temperature range of 25 to 120° C. and completes polymerization in several hours to several tens of hours may be used as a polymerization method. For example, photopolymerization that performs polymerization by applying a light beam, such as ultraviolet light or visible light, of a wavelength appropriate for activation absorption of a photoinitiator or a combination of heat polymerization and photopolymerization may be used. Note that, in this case, a tank or a chamber for polymerization may be filled with an atmosphere of an inactive gas, such as nitrogen or argon, and that polymerization may be performed in atmospheric pressure or in a pressurized state.

Figure 7A:
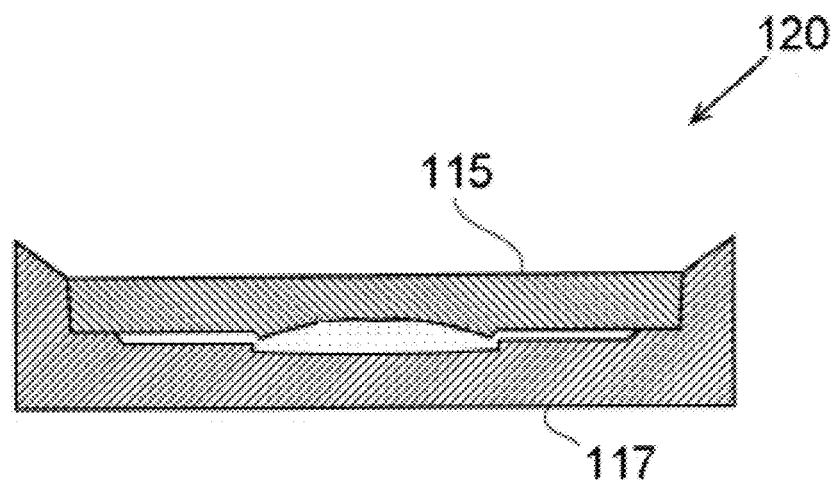
FIG. 7A is a first schematic view illustrating the molding of the bulk intraocular lens according to the one embodiment.
Figure 7B:
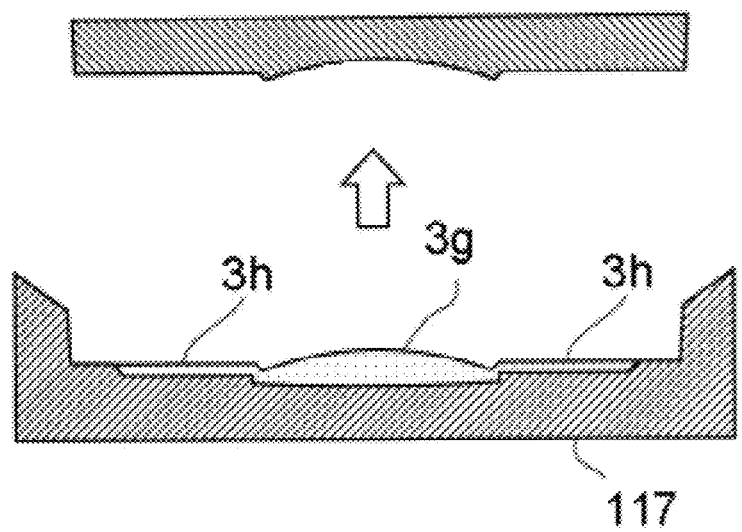
FIG. 7B is a second schematic view illustrating the molding of the bulk intraocular lens according to the one embodiment.

In the present embodiment, when polymerization of the raw material monomer 110 is completed, the upper resin mold 115 in a state in which the upper resin mold 115 and the lower resin mold 117 are brought together, as illustrated in FIG. 7A, is removed, as illustrated in FIG. 7B. With this removal, the bulk intraocular lens 3e (to be described later) is exposed. At this time, the bulk intraocular lens 3e is generally considered highly likely to remain on the lower resin mold 117 side with a larger contact area. That is, the removal of the upper resin mold 115 exposes the bulk intraocular lens 3e while the lower resin mold 117 and the bulk intraocular lens 3e are integral with each other.

Figure 8A:
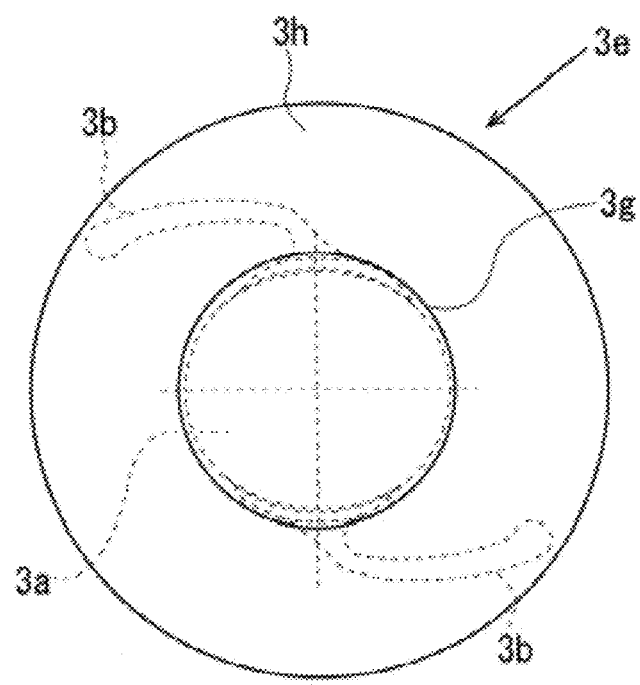
FIG. 8A is a first view illustrating a schematic configuration of the bulk intraocular lens according to the one embodiment.
Figure 8B:
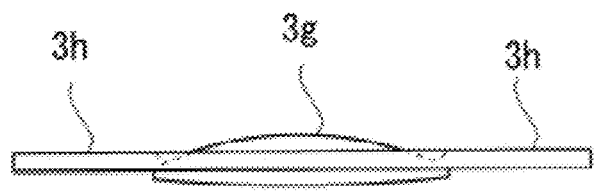
FIG. 8B is a second view illustrating a schematic configuration of the bulk intraocular lens according to the one embodiment.

As illustrated in FIG. 8A, the bulk intraocular lens 3e has an almost disk shape and includes the pre-lens body 3g that is a base for the lens body 3a and the pre-support portion 3h that is a base for the support portions 3b. The intraocular lens 2 is obtained by machining the bulk intraocular lens 3e along an outer shape of the intraocular lens 2 indicated by broken lines in FIG. 8A.

Figure 9:
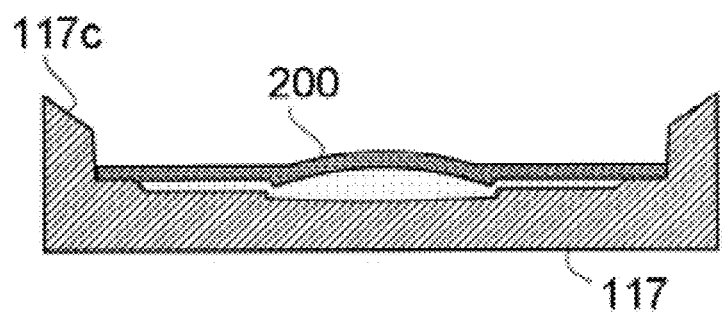
FIG. 9 is a schematic view illustrating shaping of the bulk intraocular lens according to the one embodiment.

A process for machining the bulk intraocular lens 3e to obtain the intraocular lens 2 will be described. In the present embodiment, an upper surface of the bulk intraocular lens 3e in a state in which the lower resin mold 117 and the bulk intraocular lens 3e are integral with each other, as illustrated in FIG. 7B, is covered with a coating material 200 or the like, and the bulk intraocular lens 3e is fixed, as illustrated in FIG. 9. After that, as illustrated FIGS. 10A and 10B, a conventional milling (profiling) method is used for a surface of the fixed bulk intraocular lens 3e to obtain a shape of the intraocular lens 2. At this time, air (cool air) is blown over the lens or cutting oil (e.g., a water-soluble cutting oil, such as propylene glycol, is preferable) is poured at the time of milling to prevent chip powder from being deposited as a foreign substance on a product. The desired intraocular lens 2 can be obtained by removing the coating material 200 after that. Note that any material may be adopted as the coating material 200 as long as the possibility of deposition of chip powder or dust generated when the intraocular lens 2 is cut out can be eliminated, and quality at the time of manufacture of the intraocular lens 2 can be improved. For example, a sealant, a liquid waxing compound, or the like can be used as the coating material 200.

There is no need to remove the upper resin mold 115, as illustrated in FIG. 7B. The upper resin mold 115 and the lower resin mold 117 may be processed together with the bulk intraocular lens 3e.

At the time of toric intraocular lens manufacture as well, a toric intraocular lens is obtained by polymerization using the upper resin mold 115 and the lower resin mold 117 that has a toric surface and toric marks indicating an astigmatism axis, as described earlier. In the case of a toric intraocular lens, however, a positional relationship between a toric mark and a support portion is very significant. Since if the positional relationship is not adequate the lens may break at the time of insertion or extrusion behavior may become unstable at the time of insertion to adversely influence an operation, an indicator for alignment at the time of outline machining is provided at the lower resin mold 117 to be used here in a process prior to a process of polymerization.

Toric lenses to be produced can be manufactured without lens-to-lens variation in positions of marks relative to positions of support portions by setting the lower resin mold 117 on a profiling apparatus while confirming the indicator and performing processing. An operator who performs an operation many times can perform an operation with the same sense even if a different lens is used and can obtain a stable result. Toric intraocular lenses can come in 300 or more types corresponding to the number of combinations of spherical equivalent power and cylindrical power. If marks are put on the same positions regardless of the magnitude of refractive power, cataract operations needing lenses different in refractive power can be performed with the same sense, and a stable result can be obtained. At the time of setting on the profiling apparatus, mechanical control may be performed such that the indicator is set at the same position.

Figure 10A:
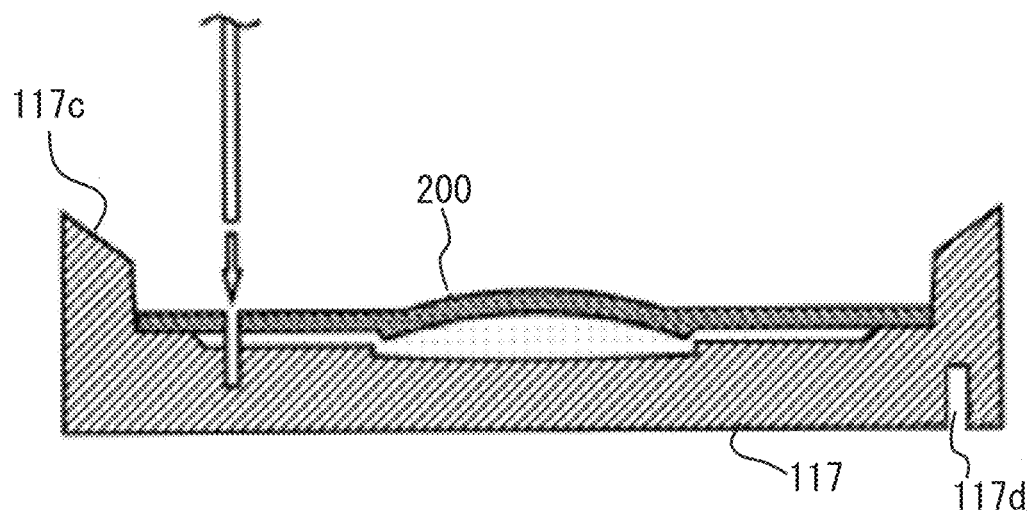
FIG. 10A is a first schematic view illustrating the shaping of the bulk intraocular lens according to the one embodiment.
Figure 10B:
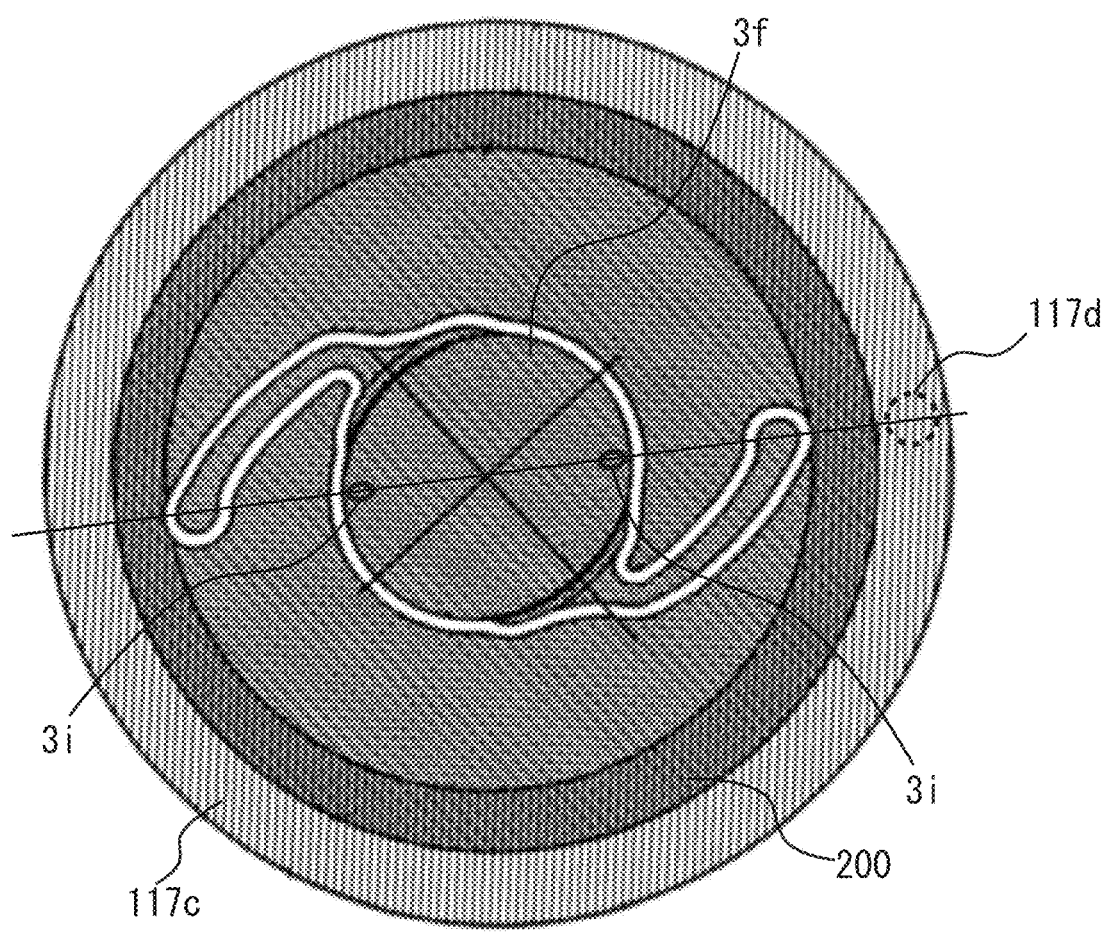
FIG. 10B is a second schematic view illustrating the shaping of the bulk intraocular lens according to the one embodiment.

An indicator for alignment will be described. As illustrated in FIGS. 10A and 10B, an indicator 117d for alignment is provided in a region where a toric lens is not to be formed and so as to fall on an extension of a toric axis indicated by intended toric mark positions (3i) on the toric surface in front view. The indicator 117d may be processed at the same time as processing of the toric surface of the lower resin mold 117 or may be implemented by adjusting the orientation of a mold for forming an indicator and the orientation of a mold for forming the toric surface at the time of molding the lower resin mold 117. The indicator 117d can be easily provided.

The indicator 117d for alignment may be provided at a position which can be observed and detected even in a polymerized state. This is because surfaces for lens formation are sandwiched between the upper resin mold 115 and the lower resin mold 117, and observation of an indicator is impossible in the polymerized state. For this reason, an indicator is preferably provided at the outer wall portion 117c (a peripheral portion of an upper surface of the lower resin mold 117) in FIG. 9 or at a surface opposite to a surface for lens formation (the indicator 117d), as illustrated in FIG. 10A. The shape of the resin mold in the present embodiment is merely an example and may be changed, as needed. For example, although the surface of the outer wall portion 117c is oblique to an optical axis of an intraocular lens, the surface may be horizontal (perpendicular to the optical axis of the intraocular lens) for easy detection of an indicator. The width of the outer wall portion 117c may be widened.

The indicator 117d desirably have a recessed shape, as illustrated in FIG. 10A. This is because if the lower resin mold 117 is rotated about the optical axis of the optical surface while a projecting component is in contact with a surface where the indicator of the lower resin mold 117 is formed, the projecting component can just fit in when the position of the projecting component coincides with that of the indicator. This configuration allows mechanical detection of an orientation with toric marks (the orientation of the toric axis). In this case, the projecting component is constructed together with an elastic body, and the height may be changed along a surface shape of the lower resin mold 117 in contact when the projecting component is in contact with a region other than a recessed portion. The recessed portion may be detected in a non-contact manner, using laser interference or the like.

The recessed portion which is to serve as the indicator may be a through-hole or a non-through-hole. In view of molding conditions and processing conditions for the resin mold, it is common to adopt a non-through-hole. In the case of a non-through-hole, a bottom surface of the recessed portion may be a surface with roughness different from that of a portion other than the recessed portion. Since a resin high in transparency is often adopted as a material for the lower resin mold 117, detection of the position of the indicator may be somewhat difficult. If the lower resin mold 117 is rotated about the optical axis of the optical surface while light, such as laser, is applied, scattering intensity of reflected light of applied light changes due to a difference in roughness between the indicator bottom surface and surroundings thereof. Detection of the indicator position is thus easier, which results in easy detection of the orientation of the toric axis. The orientation of the toric axis may be detected by performing shooting with a CCD camera or the like and image processing to obtain a difference in luminance between the optical surface and the marks. On the other hand, if the indicator has a projecting shape, since the lower resin mold 117 is often transported while a lens surface to be processed facing upward, the projecting shape interferes with a lens transport lane or a lens receiving jig, which tilts the lower resin mold 117. Since the tilt influences processing accuracy, a complicated process or an additional cost is needed to avoid the tilt.

Since a method that provides a toric surface at the lower resin mold 117 is adopted in the present embodiment, an indicator is provided at the lower resin mold 117. However, an indicator may be provided at the upper resin mold 115, depending on a manufacturing method and a configuration of a toric lens.

Figure 11A:
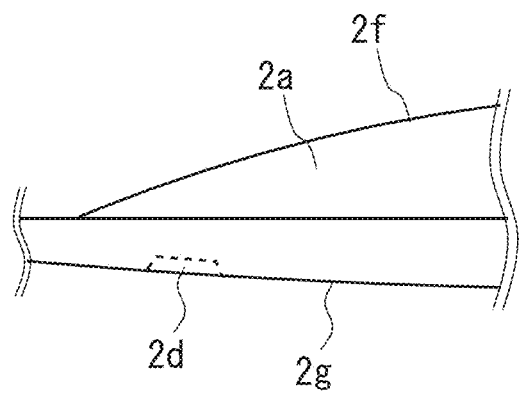
FIG. 11A is a first view illustrating a schematic configuration of a mark of the toric intraocular lens according to the one embodiment.
Figure 11B:
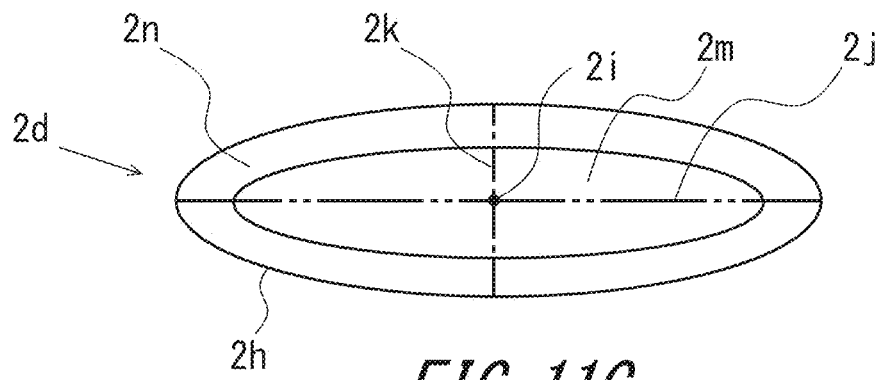
FIG. 11B is a second view illustrating a schematic configuration of a mark of the toric intraocular lens according to the one embodiment.

FIGS. 11A to 11D illustrate a schematic configuration of each mark 2d formed at the lens body 2a of the toric intraocular lens 2 according to the present embodiment. FIG. 11A is a partial enlarged view of the lens body 2a of the toric intraocular lens 2 in FIG. 1B. In the present embodiment, the mark 2d is a recessed portion which is formed at a posterior surface 2g of the lens body 2a. FIG. 11B schematically illustrates the mark 2d in top view of the lens body 2a. As illustrated in FIG. 11B, the shape of a rim 2h of the mark 2d in top view of the lens body 2a is an ellipse without an arc of a perfect circle. A major axis 2j and a minor axis 2k of the ellipse at the rim 2h which cross each other at right angles at a center 2i of gravity of the mark 2d are different in length from each other. In the present embodiment, the major axis 2j is an axis which extends in a radial direction (a direction at right angles to the optical axis 0 in the lens body 2a) of the lens body 2a, and the minor axis 2k is an axis which extends in a circumferential direction of the lens body 2a. Note that the major axis 2j corresponds to (is almost coincident with) an example (e.g., a flat meridian) of a first axis, and the minor axis 2k corresponds to a direction of an example (e.g., a steep meridian) of a second axis. The formation of the mark 2d in this manner allows reduction in the possibility of an operator mistaking the mark 2d for an air bubble or the like when the toric intraocular lens 2 is inserted into an eyeball of a patient.

A perfect circle is not formed at the rim 2h at either end of the major axis 2j. For example, if a perfect circle is formed at the rim 2h at either end of the major axis 2j, when an operator can confirm a perfect circle in question alone of the mark 2d in the toric intraocular lens inserted into an eyeball of a patient, the operator is unable to determine in which direction an astigmatic axis extends from the perfect circle in question. The mark 2d constructed such that the rim 2h does not have a perfect circle, i.e., does not have an arc of a perfect circle allows the operator to determine a direction of the astigmatic axis on the basis of the shape of the rim 2h at a portion in the vicinity of one end of the major axis 2j even in a case where the operator can confirm the portion alone.

Figure 11C:
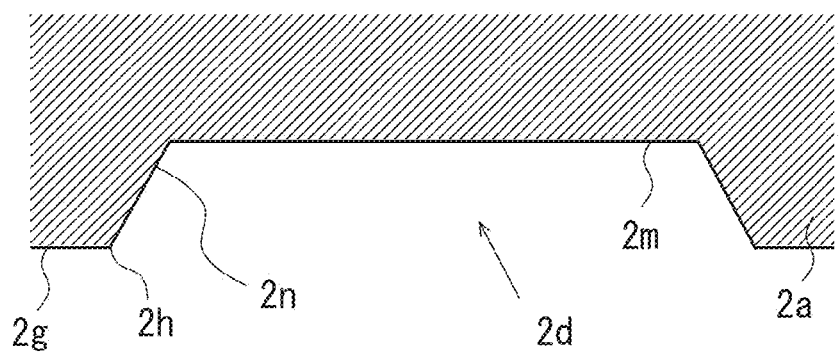
FIG. 11C is a third view illustrating a schematic configuration of a mark of the toric intraocular lens according to the one embodiment.
Figure 11D:
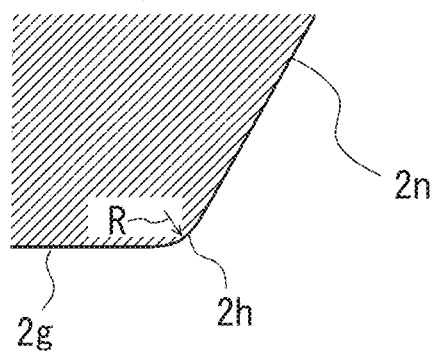
FIG. 11D is a fourth view illustrating a schematic configuration of a mark of the toric intraocular lens according to the one embodiment.

FIG. 11C schematically illustrates the mark 2d in a side cross-sectional view of the lens body 2a. As illustrated in FIG. 11C, the mark 2d has a bottom surface 2m and an inclined surface 2n which extends from the rim 2h to the bottom surface 2m. At the rim 2h of the mark 2d, the posterior surface 2g of the lens body 2a and the inclined surface 2n form an edge. FIG. 11D illustrates a partial enlarged view of the rim 2h of the mark 2d illustrated in FIG. 11C. In a cross-section of the lens body 2a (a spot including the mark 2d) along a plane parallel to the optical axis of the lens body 2a, a dimension of a radius R (also referred to as a corner radius dimension, i.e., a radial dimension of a rounded portion structurally formed at a corner portion) of a chamfer at the rim 2h is not more than a predetermined value. With this configuration, directions of refraction at the posterior surface 2g of rays of light passing through the posterior surface 2g on one side of the rim 2h as a boundary are distinctly different from directions of refraction at the inclined surface 2n of rays of light passing through the inclined surface 2n on the other side. This allows an operator to visually recognize an ellipse constituted of the rim 2h and the inclined surface 2n when the operator views the mark 2d. In the present embodiment, the predetermined value is not more than 0.1 mm (0.1 mm or a smaller dimension). It is conceivable that, if a gradient shape with an angle the posterior surface 2g forms with the inclined surface 2n which is larger than 90 degrees and smaller than 180 degrees is adopted, the operator can easily visually recognize the posterior surface 2g and the inclined surface 2n of the mark 2d from a difference in color. A toric lens having the toric mark illustrated in FIGS. 11A to 11D was actually fabricated, the IOL was inserted into an optical system which was an imitation of an aphakic eye, transmitted light was applied from a cornea side, and the optical system was observed from a retina side. In a case where the angle the posterior surface 2g forms with the inclined surface 2n was not less than 150 degrees, recognition of the boundary was impossible. From this, it is conceivable that if the toric lens is actually inserted into an eye, a patient does not recognize the boundary. The toric lens is thus desirable as an intraocular lens.

A peripheral portion (e.g., the inclined surface 2n) of the mark 2d may be adapted such that brightness changes in a stepwise manner. In this case, due to the so-called Craik-O'Brien-Cornsweet illusion, one of light passing through the posterior surface 2g and light passing through the bottom surface 2m of the mark 2d on two sides of the rim 2h and the inclined surface 2n (the peripheral portion) that change in brightness in a stepwise manner as a boundary may appear bright to an operator, and the other may appear dark to the operator. For this reason, it is conceivable that the mark 2d with the above-described configuration allows the operator to easily visually recognize the posterior surface 2g and the bottom surface 2m of the mark 2d from a difference in color or brightness.

Figure 12:
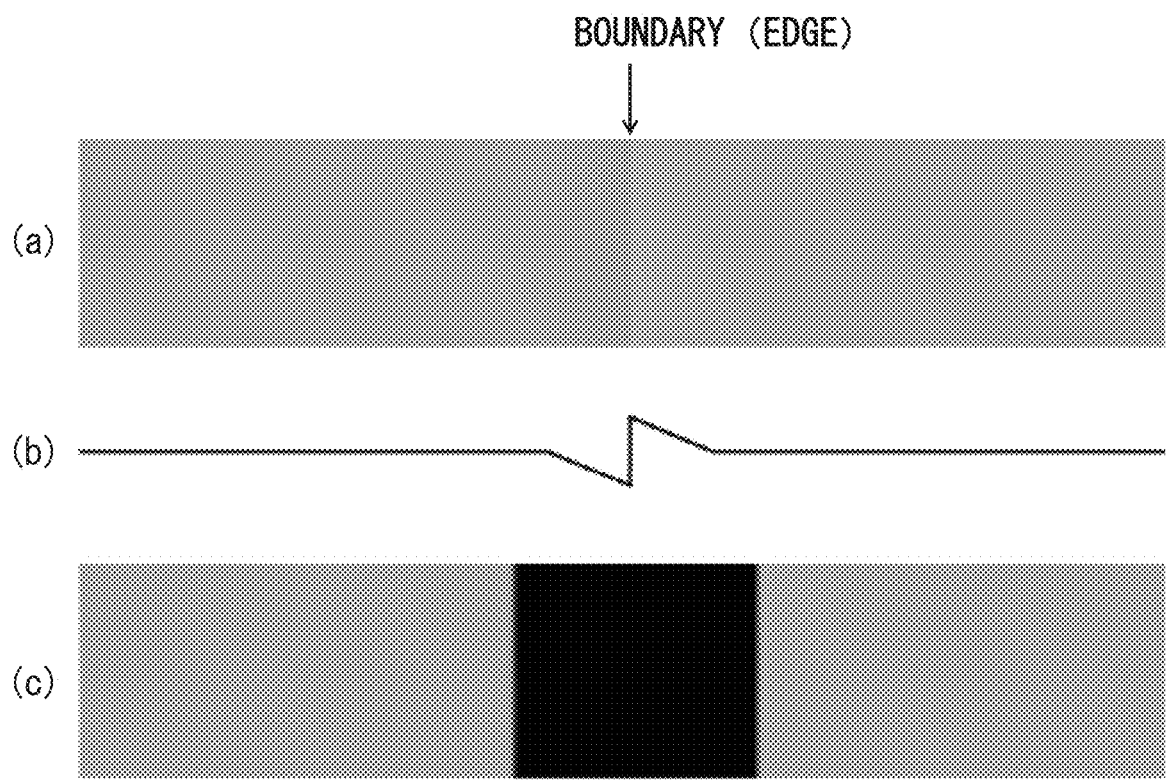
FIGS. 12(a) to 12(c) are charts illustrating one example of the Craik-O'Brien-Cornsweet illusion.

The Craik-O'Brien-Cornsweet illusion will be described with reference to FIGS. 12(a) to 12(c). In FIG. 12(a), a whole of a region on the right side of an edge at the center appears a little brighter than on the left side. FIG. 12(b) illustrates a graph with the abscissa representing a position in a region illustrated in FIG. 12(a) and the ordinate representing luminance (lightness) at each position. As indicated by the graph in FIG. 12(b), left and right regions are actually the same in brightness. FIG. 12(c) illustrates a chart of a case where a boundary portion (an edge) between the left and right regions of the region illustrated in FIG. 12(a) is filled in with black. As illustrated in FIG. 12(c), the two regions appear to have the same brightness if a central region including the edge is hidden. As described above, it is known that if a boundary portion between left and right regions with the same brightness has an edge, two sides of the edge are perceived different in brightness under influence of a brightness gradient of the edge.

A configuration which changes how light reflection appears or brightness at a boundary between a lens optical surface and a mark using effects of the illusion allows brightness recognized at the optical surface and brightness recognized at the mark to be made different and allows easier mark recognition. The illusion is produced in a case where a boundary portion has a brightness gradient. For this reason, light reflected at an edge appears brightest by forming an edge into a sharp shape at a boundary between a lens optical surface and a mark as in the present embodiment or the brightness of light reflected at a peripheral portion of the mark changes in a stepwise manner by changing roughness in a stepwise manner at the peripheral portion of the mark to implement gradient brightness. This allows effective production of the illusion and easier recognition of the mark.

The bottom surface 2m and the inclined surface 2n of the mark 2d are desirably smooth surfaces. If the bottom surface 2m and the inclined surface 2n are constructed as rough surfaces, light scattered by the bottom surface 2m and the inclined surface 2n may become stray light to influence the visual performance of a patient. In contrast, since the bottom surface 2m and the inclined surface 2n are constructed as smooth surfaces in the present embodiment, there is no risk that scattered light unnecessary for the visual performance of a patient may be generated at the bottom surface 2m and the inclined surface 2n. The smooth surfaces here refer to surfaces roughened to the extent that the bottom surface 2m and the inclined surface 2n can be regarded as almost mirror-finished surfaces. As an example, if the roughness of each of the bottom surface 2m and the inclined surface 2n of the mark 2d in the lens body 2a is not more than 20 nm (20 nm or a smaller value) (Ra) when the roughness of the optical surface except the mark 2d is not more than 5 nm (5 nm or a smaller value) (Ra) (Ra: arithmetic mean roughness), the visibility of the mark 2d can be improved without risk of generating scattered light unnecessary for the visual performance of a patient. More preferably, the roughness of each of the bottom surface 2m and the inclined surface 2n of the mark 2d is set not more than 10 nm (Ra). Alternatively, Ra for the optical surface and Ra for the mark bottom surface 2m may be made to differ by not less than 5 nm.

Additionally, the posterior surface 2g of the lens body 2a is formed as an optical surface which is a convex surface, and the mark 2d is formed as an optical surface which is a concave surface. That is, a difference in curvature generated between the mark 2d and the optical portion except the mark 2d at the posterior surface 2g of the lens body 2a can be said to contribute to improvement in the visibility of the mark 2d. Additionally, due to the so-called Hollow Face illusion, an operator recognizes the mark 2d with a concave surface formed at the posterior surface 2g of the lens body 2a as a convex surface when the toric intraocular lens 2 is inserted into an eye of a patient. As described above, it is possible to cause an operator to recognize the mark 2d as a mark with a convex surface even if the mark 2d is formed at the posterior surface 2g of the lens body 2a.

The present embodiment has been described above. Configurations of the toric intraocular lens, the intraocular lens insertion tool, and the like described above are not limited to the above-described embodiment. Various changes can be made within a range not losing identity with the technical idea of the present invention. For example, in the above description, the shapes of the rim 2h and the bottom surface 2m of the mark 2d are ellipses. Each shape may be an oblong or a polygon having a short side and a long side, such as a rectangle, in addition to an ellipse. Although the mark 2d is a recessed portion formed at the posterior surface 2g of the lens body 2a in the embodiment, a projecting portion formed at the anterior surface 2f of the lens body 2a may be used instead of the mark 2d. Although the mark 2d is composed of the bottom surface 2m and the inclined surface 2n, the bottom surface 2m and the inclined surface 2n may be constructed as curved surfaces. The recessed shape of the indicator 117d may be any shape, such as a through-hole, a non-through-hole, a groove, or a notch, or the indicator may be created by a method other than forming the indicator into a recessed shape, such as paint, printing, or surface roughening. An intraocular lens, on which a mark according to the present invention is to be put, may not be a one-piece lens and may be a so-called three-piece intraocular lens in which support portions and a lens portion are composed of different materials or members.

Figure 13A:
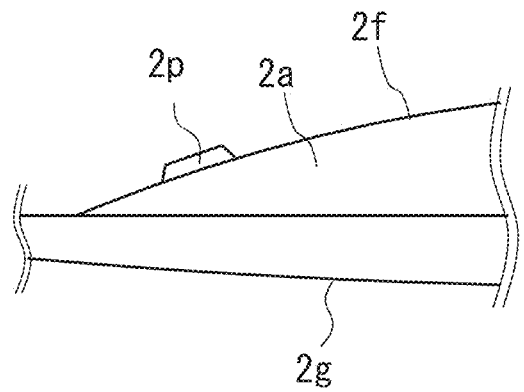
FIG. 13A is a first view illustrating a schematic configuration of a mark of the toric intraocular lens according to one modification.
Figure 13B:
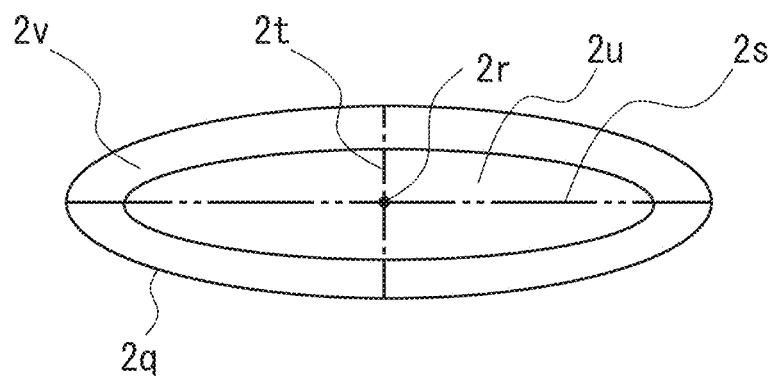
FIG. 13B is a second view illustrating a schematic configuration of a mark of the toric intraocular lens according to one modification.
Figure 13C:
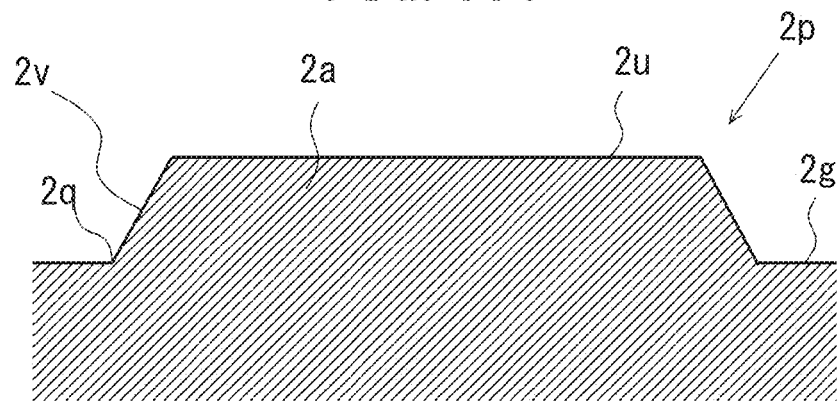
FIG. 13C is a third view illustrating a schematic configuration of a mark of the toric intraocular lens according to one modification.

FIGS. 13A to 13C illustrate a schematic configuration of a mark 2p which is formed at the anterior surface 2f of the lens body 2a instead of the mark 2d formed at the posterior surface 2g of the lens body 2a. FIG. 13A is a partial enlarged view of the lens body 2a of the toric intraocular lens 2 in FIG. 1B. The mark 2p is a projecting portion which is formed at the anterior surface 2f of the lens body 2a. FIG. 13B schematically illustrates the mark 2p in top view of the lens body 2a. As illustrated in FIG. 13B, the shape of a rim 2q of the mark 2p is an ellipse. That is, a major axis 2s extending in the radial direction of the lens body 2a and a minor axis 2t extending in the circumferential direction of the lens body 2a which cross each other at a center 2r of gravity of the mark 2p are different in length from each other. A perfect circle is not formed at the rim 2q at either end of the major axis 2s.

FIG. 13C schematically illustrates the mark 2p in a side cross-sectional view of the lens body 2a. As illustrated in FIG. 13C, the mark 2p has an upper surface 2u and an inclined surface 2v which extends from the rim 2q to the upper surface 2u. At the rim 2q of the mark 2p, the anterior surface 2f of the lens body 2a and the inclined surface 2v form an edge. Thus, the formation of the mark 2p that is a projecting portion at the anterior surface 2f of the lens body 2a can be said to allow an operator to easily visually recognize the anterior surface 2f and the mark 2p by a difference in color, like a case where the mark 2d is formed at the posterior surface 2g of the lens body 2a.

Figure 14A:
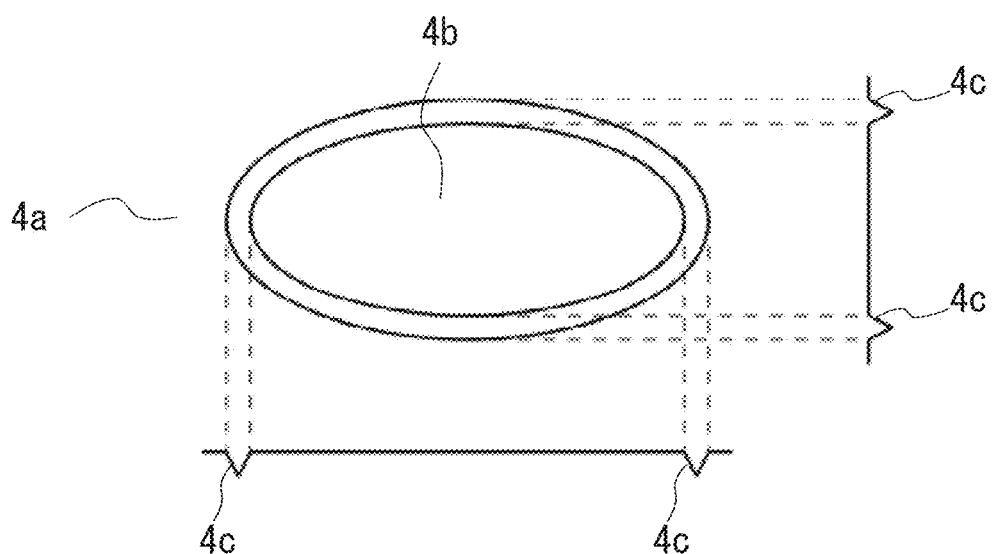
FIG. 14A is a first view illustrating a schematic configuration of a mark of the toric intraocular lens according to one modification.
Figure 14B:
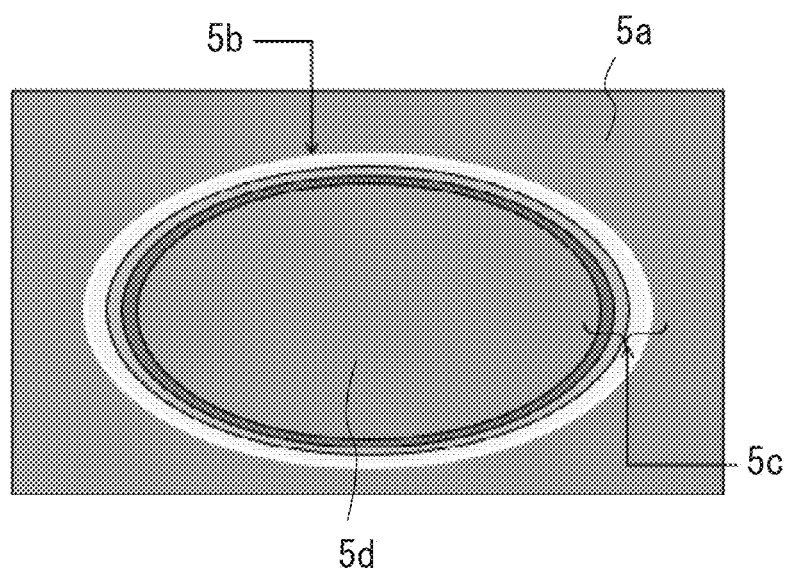
FIG. 14B is a second view illustrating a schematic configuration of a mark of the toric intraocular lens according to one modification.

As another aspect that changes how light reflects at a boundary between a mark and an optical portion, a shape with a inclined portion 4c solely at a boundary between an optical portion 4a and a mark 4b on an optical surface of a lens body may be adopted, as illustrated in FIG. 14A. Alternatively, a transitional portion 5c which changes in roughness in a stepwise manner between a mark 5d and a rim 5b of the mark 5d may be provided without providing a significant level difference at a boundary between an optical portion 5a and the mark 5d on an optical surface of a lens body, as illustrated in FIG. 14B.

A modification of an indicator for alignment will be described. In the present modification, a recessed portion with φ=2.0 mm was provided in a lower resin mold at a peripheral portion of an optical surface on a side opposite to a side with a toric surface. Outline machining was performed using the recessed portion as an indicator. A lower resin mold without an indicator as a control was also fabricated, and alignment accuracies were compared. Since an astigmatic axis was hard to perceive in a polymerized state in the case without an indicator, a mark of the position of a toric mark at an optical surface needed to be put on the lower resin mold with an oil-based pen after the toric mark is searched for under a microscope using telecentric transmitted illumination. The lower resin mold was set on a processing machine using the mark as an indicator, and outline machining was performed. As a result, the lower resin mold having the recessed portion with φ=2.0 mm allowed high-accuracy alignment. In the present modification, indicator detection by visual inspection and manual setting on the processing machine were performed. It is easily conceivable that mechanical indicator detection and mechanical setting on a processing machine allow higher-accuracy alignment.

In a case where a part of a resin mold is formed into a so-called D cut shape instead of using an indicator in order to detect a toric axis or in other cases, a D-cut position may be asymmetrical with respect to a flow of resin, and the flow of resin may be impaired to cause a molding failure. However, in the present modification, no change was found by examination of an optical surface using an interferometer, and it was confirmed that an indicator did not cause a molding failure.

REFERENCE SIGNS LIST 1 intraocular lens insertion tool
2 toric intraocular lens
2a lens body
2d, 2p mark

What is claimed is:

1. A toric intraocular lens comprising a lens body provided with an astigmatic axis,
wherein a mark indicating the astigmatic axis is formed at an optical surface of the lens body, and
the mark is formed of only one single recessed portion and has a shape that is line-symmetrical with respect to a first axis coinciding with the astigmatic axis and is line-symmetrical with respect to a second axis being orthogonal to the first axis, in top view of the optical surface, wherein the shape is defined by a rim of the mark, and
a length of an external dimension of the mark in a direction of the first axis is different from a length of the external dimension of the mark in a direction of the second axis,
wherein the mark is an indentation that includes a bottom surface and an inclined surface,
the bottom surface corresponds to a bottom surface of the recessed portion and is substantially parallel to the optical surface of the lens body, and
the inclined surface is adjacent to the rim and extends from the rim to the bottom surface of the mark in a cross-section of the lens body along a plane parallel to an optical axis of the lens body.

2. The toric intraocular lens according to claim 1, wherein a contour of the rim of the mark at least on one end side of the first axis in the mark does not have an arc of a perfect circle.

3. The toric intraocular lens according to claim 1, wherein the mark is formed at a posterior surface of the lens body.

4. The toric intraocular lens according to claim 1, wherein a radial dimension of a chamfer at the rim of the mark in a cross-section of the lens body along the plane parallel to the optical axis of the lens body is 0.1 mm or a smaller dimension.

5. The toric intraocular lens according to claim 1, wherein a value of surface roughness of the mark is 20 nm or a smaller value, and surface roughness of the optical surface is different from the surface roughness of the mark.

6. The toric intraocular lens according to claim 1, wherein the toric intraocular lens comprises a toric intraocular lens group that is composed of a plurality of toric intraocular lenses having different refractive powers of lens bodies of the plurality of toric intraocular lenses with each other, and
a mark as same as the mark defined in claim 1 is mark is provided at a fixed position relative to a position of a support portion of the toric intraocular lens in each of the toric intraocular lenses in the toric intraocular lens group, regardless of the refractive powers of the lens bodies of the plurality of toric intraocular lenses.

7. The toric intraocular lens according to claim 1, wherein the inclined surface is inclined linearly from the rim to the bottom surface of the mark.

\* \* \* \* \*

UNITED STATES PATENT AND TRADEMARK OFFICE
CERTIFICATE OF CORRECTION

| | |
|---|---|
| PATENT NO. | : 11,622,851 B2 |
| APPLICATION NO. | : 16/309903 |
| DATED | : April 11, 2023 |
| INVENTOR(S) | : Haruo Ishikawa |

It is certified that error appears in the above-identified patent and that said Letters Patent is hereby corrected as shown below:

In the Claims

Column 18, Line 66, Claim 6, delete "is mark".

Signed and Sealed this
Fifteenth Day of August, 2023

Katherine Kelly Vidal
*Director of the United States Patent and Trademark Office*